(12) United States Patent
Warner

(10) Patent No.: US 7,199,263 B2
(45) Date of Patent: Apr. 3, 2007

(54) ACETIC ANHYDRIDE AND ACETATE ESTER CO-PRODUCTION

(75) Inventor: R. Jay Warner, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 322 days.

(21) Appl. No.: 10/920,688

(22) Filed: Aug. 18, 2004

(65) Prior Publication Data

US 2006/0041162 A1    Feb. 23, 2006

(51) Int. Cl.
*C07C 67/08* (2006.01)
*C07C 51/54* (2006.01)

(52) U.S. Cl. ...................... 560/239; 562/892

(58) Field of Classification Search ................ 560/231, 560/232, 239, 248; 562/887, 888, 892
See application file for complete search history.

(56) References Cited

U.S. PATENT DOCUMENTS

| | | | | |
|---|---|---|---|---|
| 2,232,705 A | * | 2/1941 | Hull ........................... | 562/892 |
| 2,820,058 A | * | 1/1958 | Luke, Jr. et al. ............ | 568/302 |
| 4,455,439 A | * | 6/1984 | Arnold et al. ............... | 568/302 |
| 4,481,146 A | | 11/1984 | Leupold et al. ............. | 260/410 |
| 4,737,318 A | | 4/1988 | Ichino et al. ................ | 260/547 |
| 5,264,087 A | * | 11/1993 | Lowery et al. ............... | 203/80 |
| 5,998,658 A | | 12/1999 | Wu et al. .................... | 560/239 |
| 6,028,215 A | | 2/2000 | Bessling et al. ............. | 560/265 |
| 6,458,992 B1 | * | 10/2002 | Lederer et al. ............. | 560/239 |
| 6,693,213 B1 | | 2/2004 | Kolena et al. ............... | 560/265 |
| 2001/0029309 A1 | | 10/2001 | Nishioka et al. ............ | 568/617 |

FOREIGN PATENT DOCUMENTS

JP            41021981        10/1966

\* cited by examiner

*Primary Examiner*—Karl Puttlitz
(74) *Attorney, Agent, or Firm*—M. Susan Spiering

(57) ABSTRACT

A method of co-producing acetic anhydride and an acetate ester includes pyrolizing acetic acid at elevated temperature to produce a first ketene stream, the first ketene stream being a vapor phase stream comprising ketene, acetic acid and water; cooling the first ketene stream to condense acetic acid and water therefrom, thereby generating (i) a weak acid aqueous stream and (ii) a ketene feed stream; feeding the ketene feed stream to an acetic anhydride reactor where the ketene is reacted with acetic acid to produce acetic anhydride; concurrently with step (c), feeding the weak acid aqueous stream to an esterification reactor wherein acetic acid in the weak acid stream is reacted with an organic alcohol to produce an acetate ester. Preferably, the organic alcohol is selected from organic alcohols which (i) form acetate esters which esters and optionally alcohols provide azeotropic mixtures with water and (ii) wherein the azeotropic mixtures have a water content greater than the amount of water generated by reaction of the alcohol with acetic acid to facilitate azeotropically separating the acetate ester from the reaction mixture.

20 Claims, 1 Drawing Sheet

ACETIC ANHYDRIDE AND ACETATE ESTER CO-PRODUCTION

FIELD OF THE INVENTION

The present invention is directed generally to co-production of acetic anhydride and acetate esters. More specifically, there is provided in accordance with the present invention a method of producing acetic anhydride by a ketene process, generating a weak acid stream and utilizing the weak acid stream for ester production

BACKGROUND OF THE INVENTION

The production of acetic anhydride, by the ketene process, is well known. The method comprises: the thermal decomposition of acetic acid at high temperatures utilizing, for example, a triethyl phosphate dehydration catalyst to produce ketene (I), which is subsequently reacted with excess acetic acid to obtain acetic anhydride (II):

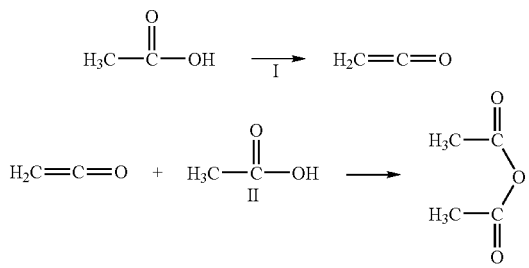

The first step of the process is conducted at low pressure and elevated temperature, typically in excess of 700° C. Catalyst in the product stream may be neutralized with ammonia. The process is widely employed; however, it is capital intensive especially because water generated in step I needs to be removed and acetic acid needs to be removed and recovered. In other words, weak acid recovery adds significantly to the required capital and also impacts operating energy costs adversely. Representative references relating to various aspects of acetic anhydride and ketene production are discussed briefly below.

U.S. Pat. No. 4,455,439 to Hoechst AG, Jun. 19, 1984, describes a process for the preparation of ketene by the thermal, catalytic cracking of acetic acid under reduced pressure. The hot cracked gasses are then cooled to 0° to −10° C. and water, unreacted acetic acid, and acetic anhydride are condensed.

U.S. Pat. No. 4,737,318 to Daicel Chemical Industries, Apr. 12, 1988, describes a process for recovering acetic anhydride from an aqueous solution containing acetic anhydride and acetic acid, which comprises a condensate obtained in a step of cooling a decomposition gas formed in the production of ketene by pyrolyzing acetic acid and cooling the formed gas.

A continuous process for refining acetic anhydride produced by the reaction of ketene and acetic acid is described in U.S. Pat. No. 5,264,087 to Eastman Kodak, Nov. 23, 1993. The process involves a vacuum distillation step, which results in the production of high purity acetic anhydride.

U.S. Patent Application No. 2001/0029309 to Nishioka et al. describes a further purification step in which distilled acetic anhydride is treated with ozone to reduce the diketene content.

Another method for reducing diketene in purified acetic anhydride, described in Japanese Patent No. 41021981 to Nihon Gosei Company, consists of heating the reaction liquid in the presence of diketene polymerization catalysts such as an alkali metal hydroxide alcoholate, sodium acetate, or organic bases.

The production of alkyl esters of acetic acid, from various alkanols, is also well known. Here again, water removal is a significant component of capital and operating expense. Some representative patents are discussed immediately below.

U.S. Pat. No. 4,481,146 to Hoechst AG, Nov. 6, 1984, describes a process for the preparation of an ethyl ester from ethanol-containing mixtures of aliphatic alcohols, which comprises esterifying the alcohols with a carboxylic acid in the presence of an acid catalyst in a distilling column and separating in the same column the ethyl ester continuously from the ester mixture obtained.

A method for making esters of acetic acid, which is a catalytic distillation process utilizing solid acidic catalysts for the esterification of acetic acid with alcohols is described in U.S. Pat. No. 5,998,658 to Industrial Technology Research Institute, Dec. 7, 1999.

U.S. Pat. No. 6,028,215 to BASF AG, Feb. 22, 2000, describes a process for preparing esters from alcohol and carboxylic acid by feeding a mixture of alcohol and carboxylic acid into a distillation column with separated sections containing reactive and conventional internals, reaction of the alcohol and the carboxylic acid in the reactive internals in the presence of a heterogeneous catalyst, distillative separation of the evolving reaction mixture into the higher boiling ester and a lower boiling azeotrope containing alcohol, water and ester, and separation of the azeotrope in a phase separator.

U.S. Pat. No. 6,458,992 to Sulzer Chemtech AG, Oct. 1, 2002, relates to a process for the synthesis of butyl acetate by esterification of acetic acid with butanol by combined distillation and chemical reaction utilizing a column in which separation of the reaction products takes place together with the esterification in catalytically active separation equipment.

U.S. Pat. No. 6,693,213 to Sulzer Chemtech AG, Feb. 17, 2004, describes a method of ethyl acetate synthesis by esterification of acetic acid with ethyl alcohol or by reaction of acetic anhydride with ethyl alcohol, which uses catalytic distillation in a column, during which a reaction on a catalytically active filling and a rectification and separation of reaction products take place simultaneously.

In any event, there is a need in the art to reduce capital required for purification and to increase yields as well as operating efficiency. The present invention meets these needs by concurrently producing acetic anhydride and acetate esters utilizing integrated production equipment.

SUMMARY OF THE INVENTION

The process of the present invention generates an acetic acid aqueous stream in connection with anhydride production and uses that weak acid stream for producing acetate esters. Water need not be removed prior to feeding the weak acid stream to the esterification unit, reducing overall purification investment. Moreover, in especially preferred cases the water in the weak acid stream provided to the esterification unit has a beneficial effect for azeotropic separation. These especially preferred cases are those where the acetate ester/water azeotrope has a higher water content than the stoichiometric amount of water produced by esterification with the organic alcohol. Butyl acetates are particularly preferred co-products as will become apparent from the detailed description provided hereinafter.

There is thus provided in accordance with the present invention a method of co-producing acetic anhydride and an acetate ester including: pyrolizing acetic acid at elevated temperature to produce a first ketene stream, the first ketene stream being a vapor phase stream comprising ketene, acetic acid and water; cooling the first ketene stream to condense acetic acid and water therefrom, thereby generating (i) a weak acid aqueous stream and (ii) a ketene feed stream; feeding the ketene feed stream to an acetic anhydride reactor where the ketene is reacted with acetic acid to produce acetic anhydride; and concurrently with step (c), feeding the weak acid aqueous stream to an esterification reactor wherein acetic acid in the weak acid stream is reacted with an organic alcohol to produce an acetate ester. Typically, the organic alcohol is selected from organic alcohols which form acetate esters which esters and optionally alcohols provide azeotropic mixtures with water; and preferably the organic alcohol is selected from the group consisting of methanols, ethanols, propanols and butanols. In the most preferred embodiments, the organic alcohol is selected from organic alcohols which (i) form acetate esters which esters and optionally alcohols provide azeotropic mixtures with water; and (ii) wherein the azeotropic mixtures have a water content greater than the water generated by reaction of the alcohol with acetic acid. Preferred alcohols include n-butanol, s-butanol and i-butanol.

Optionally, the process further includes the step of flashing the weak acid stream prior to feeding it to the esterification reactor, thereby supplying vapor phase acetic acid and steam to the esterification reactor and concurrently removing by-products. The pyrolysis step may be catalyzed by (i) a phosphate catalyst which is subsequently neutralized with ammonia or (ii) an ammonium phosphate catalyst. One preferred dehydration catalyst is triethyl phosphate, and another is diammonium phosphate. The process may also include addition of a strong acid, such as phosphoric acid, to the flashing step to minimize decomposition of the ammonium salts contained in the weak acid stream.

Generally, the weak acid aqueous stream has an acid content of from about 10 to about 90 weight percent; typically, the weak acid aqueous stream has an acid content of from about 30 to bout 70 weight percent; and preferably the weak acid aqueous stream has an acid content of from about 40 to about 60 weight percent. The step of pyrolizing the acetic acid is generally carried out at a temperature of from about 680° C. to about 750° C. In one embodiment, the ketene is reacted with acetic acid in the presence of ammonia.

One preferred process is a method of co-producing acetic anhydride and an acetate ester comprising: pyrolizing acetic acid at elevated temperature to produce a first ketene stream, the first ketene stream being a vapor phase stream comprising ketene, acetic acid and water; cooling the first ketene stream to condense acetic acid and water therefrom, thereby generating (i) a weak acid aqueous stream and (ii) a ketene feed stream; feeding the ketene feed stream to an acetic anhydride reactor where the ketene is reacted with acetic acid to produce acetic anhydride; concurrently with step (c), feeding the weak acid aqueous stream to an esterification reactor wherein acetic acid in the weak acid stream is reacted with an organic alcohol to produce an acetate ester in an esterification medium, wherein the organic alcohol forms acetic acid esters which esters and optionally alcohols provide azeotropic mixtures with water; and azeotropically separating the acetate ester so formed from the esterification medium.

Another preferred process is a method of co-producing acetic anhydride and an acetate ester comprising: pyrolizing acetic acid at elevated temperature to produce a first ketene stream, the first ketene stream being a vapor phase stream comprising ketene, acetic acid and water; cooling the first ketene stream to condense acetic acid and water therefrom, thereby generating (i) a weak acid aqueous stream and (ii) a ketene feed stream; feeding the ketene feed stream to an acetic anhydride reactor where the ketene is reacted with acetic acid to produce acetic anhydride; concurrently with step (c), feeding the weak acid aqueous stream to an esterification reactor wherein acetic acid in the weak acid stream is reacted with an organic alcohol to produce an acetate ester in an esterification medium, wherein the organic alcohol is selected from organic alcohols which (i) form acetate esters which esters and optionally alcohols provide azeotropic mixtures with water and (ii) wherein the azeotropic mixtures have a water content greater than the amount of water generated by reaction of the alcohol with acetic acid; and azeotropically separating the acetate ester so formed from the esterification medium.

BRIEF DESCRIPTION OF THE DRAWINGS

The process of the invention is illustrated and described in connection with FIG. 1 which is a schematic diagram illustrating the process of the invention.

DETAILED DESCRIPTION OF THE INVENTION

Figure 1:
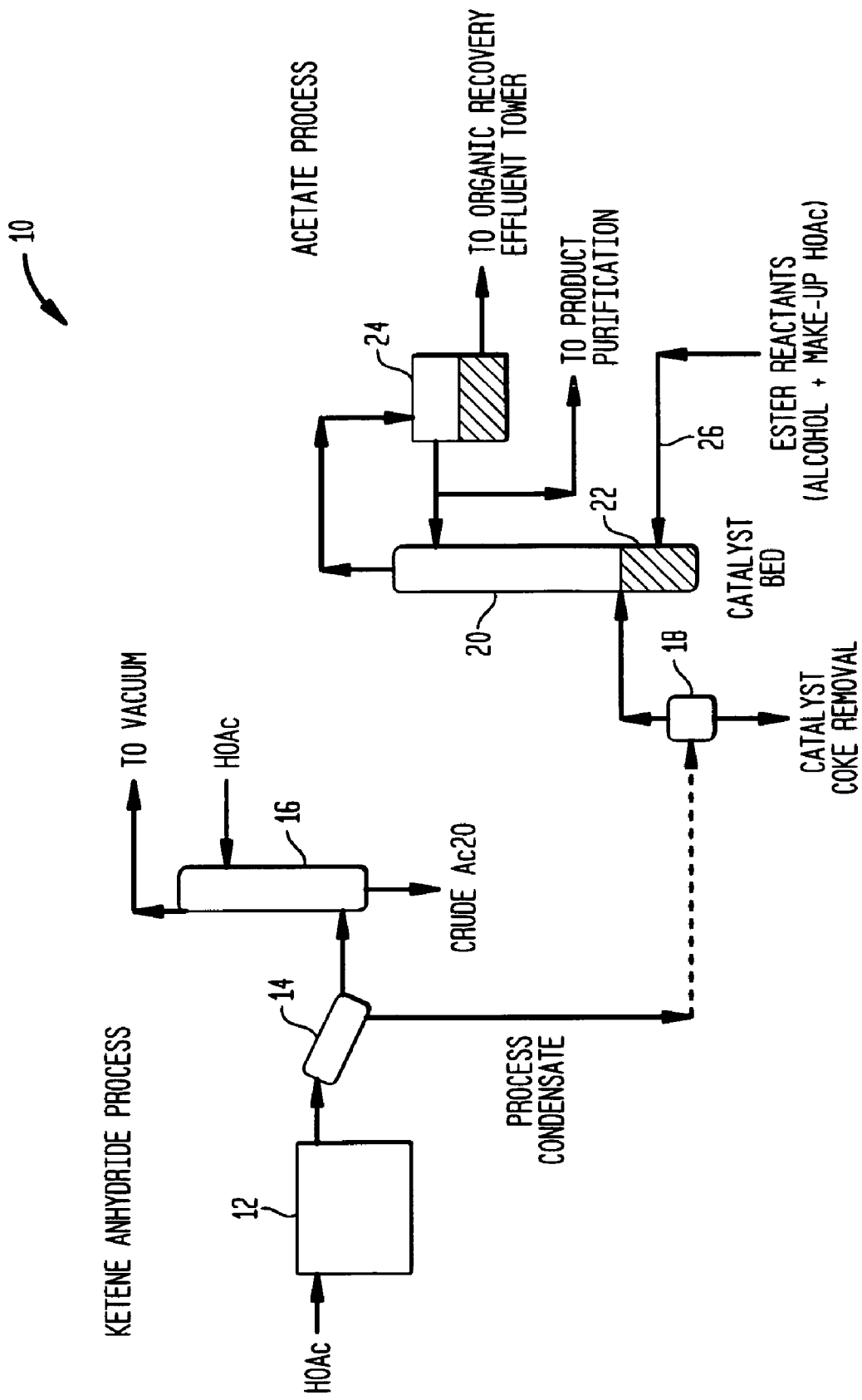

The invention is described in detail below in connection with particular features. Modifications within the spirit and scope of the present invention, set forth in the appended claims, will be readily apparent to those of skill in the art.

As previously explained, the production of acetic anhydride, by the ketene process, is well known. The method comprises: pyrolysis of acetic acid at high temperatures utilizing a dehydration catalyst to produce ketene (I), which is subsequently reacted with excess acetic acid to obtain acetic anhydride (II):

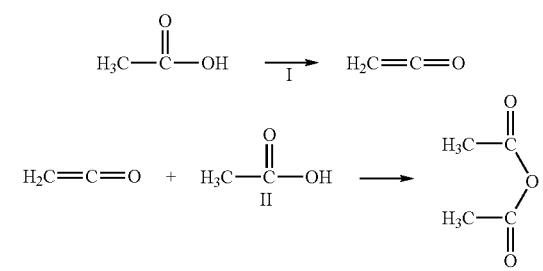

Step I also produces 1 mol of water per mol of ketene as will be appreciated from the stoichiometry of the reaction. The heat of reaction is approximately 147 kJ/mol. Optimum yields of ketene require a temperature of about 680–750° C. Low pressure increases the yield, but not the efficiency of the process. Triethyl phosphate is commonly used as dehydration catalyst for the water formed in the first step. It is neutralized in the exit gases with ammonia. Compression of ketene using the liquid-ring pump substantially improves the formation of anhydride. Nickel-free alloys, e.g., ferrochrome alloy, chrome-aluminum steel, are needed for the acetic acid pyrolysis tubes, because nickel promotes the formation of soot and coke, and reacts with carbon monoxide yielding a highly toxic metal carbonyl. Coke formation is a serious efficiency loss. Conventional operating conditions furnish 85–88% conversion, selectivity to ketene 90–95 mol %.

Instead of triethyl phosphate, diammonium phosphate may be used as the dehydration catalyst.

Acetate ester manufacture is also well known. Typically, acetic acid is reacted in the liquid phase with an organic alcohol utilizing an acid catalyst such as mineral acid or a cationic strong acid ion-exchange resin. Here again, 1 mol of water is formed per mol of product ester. The process includes rectifying crude product in many cases as an azeotrope with water. Removal of ester/water azeotropes from the reaction mixture drives the equilibrium in favor of the ester product. Selected azeotrope compositions of acetate esters are set forth below in Table A.

TABLE A

Stoichiometric Amount of Water Generated and Azeotrope Water Amount for Selected Acetate Esters

| ESTER Acetate | % WATER Stoich. | Azeotrope |
|---|---|---|
| Methyl | 19.5% | 3.2% |
| Ethyl | 17.0% | 8.7% |
| iPropyl | 15% | 14.0% |
| nPropyl | 15.0% | 14.0% |
| nButyl | 13.4% | 28.7% |
| iButyl | 13.4% | 16.5% |
| sButyl | 13.4% | 22.5% |

"Azeotropically separating" and like terminology refers to separating the product acetate ester from a reaction mixture with water, reactants and catalyst and by vaporizing an azeotrope of the product acetate ester and water. The azeotrope optionally includes alcohol reactant. Such separation uses to advantage the low boiling point of the ester/water azeotrope to drive the equilibrium to product ester.

The production of ethyl acetate by continuous esterification is an example of the use of azeotropic principles to obtain a high yield of ester. The acetic acid, concentrated sulfuric acid, and an excess of 95% ethyl equilibrium is reached in the mixture, it is pumped into a receiving tank and through a preheater into the upper section of a bubblecap plate column. The temperature at the top of this column is maintained at a ca 80° C. and its vapor (alcohol with the ester formed and ca 10% water) is passed to a condenser. The first recovery column is operated with a top temperature of 70° C., producing a ternary azeotrope of 83% ester, 9% alcohol, and 8% water. The ternary mixture is fed to a static mixer where water is added in order to form two layers and allowed to separate in a decanter. The upper layer contains ca 93% ethyl acetate, 5% water, and 2% alcohol, and is sent to a second recovery or ester-drying column. The overhead from this column is 95–100% ethyl acetate which is sent to a cooler and then to a storage tank.

There is indicated schematically in FIG. 1 an apparatus 10 for practicing the present invention. Apparatus 10 includes a ketene furnace 12 coupled to a chiller train 14 which, in turn, communicates with an anhydride reactor 16 and a flasher 18. Flasher 18 has an output to an esterification reaction tower 20 which has a catalyst bed 22 of cationic strong acid ion exchange resin. Tower 18 is coupled to a decanter 24.

In order to practice the inventive process, acetic acid and catalyst is fed to furnace 12 where the acetic acid is thermally decomposed to ketene and water at temperatures of about 680–750° C. Thereafter, the hot gas is cooled in chiller train 14.

Chiller train 14 condenses water and acetic acid from the hot furnace gases and feeds flasher 18 with the condensate, while the uncondensed output from the furnace is fed to anhydride reactor 16 as shown in FIG. 1. In reactor 16, the ketene is reacted with additional acetic to produce acetic anhydride. Crude anhydride is removed as liquid, while overhead may be further purified and recycled or otherwise utilized.

The process condensate stream from the ketene anhydride process chiller train primarily contains acetic acid, water, acetic anhydride, and non-volatiles including phosphorus-containing catalyst (e.g., ammonium phosphates) and carbon (from ketene decomposition and furnace coking). The acetic anhydride subsequently reacts with the water present in the process condensate stream to form acetic acid. This process condensate stream is preferably conditioned or purified to exclude impurities that could adversely affect the quality of acetate esters produced from the acetic acid contained in the stream, and to remove compounds that could neutralize the catalyst used for esterification of acetic acid and an alcohol in the co-production of acetate esters. In some cases the condensed furnace output, or weak acid stream may contain unwanted ammonia salts in the form of acetates. These salts are potential sources of unwanted by-products and accordingly are minimized advantageously by adding a mineral acid such as phosphoric acid to the condensate prior to the flashing step While ketene is fed to reactor 16, flasher 18 reboils the condensate from the chiller train, which is, as noted above, a weak acid stream having a typical composition of roughly 50/50 acetic acid/water. The vaporized acetic acid and steam is fed to esterification reaction tower 20 concurrently with the supply of ketene to reactor 16. Solids and heavier components are thus removed from the weak acid stream by the flasher prior to feeding the stream to the esterification tower.

Reactor 20 is also fed with additional acetic acid and organic alcohol at 26. The reaction mixture is converted to acetate ester in reactor 20; the reaction being catalyzed by bed 20. Ester product is separated from the reaction medium at a lower end of the tower by distillation, preferably involving an azeotrope as noted above. The output of power 20 is decanted at 24.

Some of the crude ester is refluxed to tower 20, while crude product is also drawn off for further purification.

The invention thus provides considerable advantages over conventional manufacturing methods. For one, water by-product from ketene manufacture is processed by way of the esterification process equipment, leading to considerable savings in terms of capital since recovery equipment need not be duplicated. For another, the co-production process of this invention makes it possible to use water by-product of ketene manufacture to azeotrope esters whose manufacture does not generate enough water stoichiometrically to azeotropically separate the product from the reaction medium in tower 20. In such cases, water is conventionally added separately, increasing operating costs. On the other hand, the invention uses an available weak acid stream as both a water source and a source of acetic acid. A specific example follows.

EXAMPLE

Process condensate obtained from a ketene furnace such as furnace 12 and a chiller train such as train 14 was continuously fed to a laboratory flasher apparatus consisting of a 0.5 liter electrically-heated reboiler attached to a vacuum-jacketed vapor-liquid disengagement section that directed vapors to a condenser and to a receiving vessel to collect liquid condensed from the overhead vapor stream. A process condensate sample containing about 61.3 wt % acetic acid, 38.2 wt % water, and 0.5 wt % non-volatiles was fed to the flasher apparatus while taking about 97.2% (w/w) of the feed as flasher distillate under atmospheric pressure conditions.

The flashed process condensate was analyzed to contain about 61.6 wt % acetic acid and 38.4 wt % water, and was then fed to the catalyst bed a 45-tray Oldershaw n-butyl acetate reaction tower (e.g. a tower such as tower 20). The homogeneous catalyst bed contained 1+/−0.3 wt % methane sulfonic acid. Overhead vapors from the reaction tower were condensed and formed two phases in an overhead decanter (e.g. a decanter such as decanter 24). The n-butyl acetate rich, top layer from the decanter was refluxed to the top tray to produce a crude product stream that, for example, contained ~97.8 wt % n-butyl acetate, 1.1 wt % n-butanol, 1.1 wt % water and only a trace of acetic acid. The aqueous-rich lower phase was pumped from the decanter.

While the invention has been described in connection with several examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A method of co-producing acetic anhydride and an acetate ester comprising:
   (a) pyrolizing acetic acid at elevated temperature to produce a first ketene stream, the first ketene stream being a vapor phase stream comprising ketene, acetic acid and water;
   (b) cooling the first ketene stream to condense acetic acid and waler therefrom, thereby generating
      (i) a weak acid aqueous stream and
      (ii) a ketene feed stream;
   (c) feeding the ketene feed stream to an acetic anhydride reactor where the ketene is reacted with acetic acid to produce acetic anhydride; and
   (d) concurrently with step (c), feeding the weak acid aqueous stream to an esterification reactor wherein acetic acid in the weak acid stream is reacted with an organic alcohol to produce an acetate ester.

2. The method according to claim 1, wherein the organic alcohol is selected from organic alcohols which form acetate esters which esters and optionally alcohols provide azeotropic mixtures with water.

3. The method according to claim 2, wherein the organic alcohol is selected from the group consisting of methanols, ethanols, propanols and butanols.

4. The method according to claim 2, wherein the organic alcohol is selected from organic alcohols which
   (i) form acetate esters which esters and optionally alcohols provide azeotropic mixtures with water; and
   (ii) wherein the azeotropic mixtures have a water content greater than the water generated by reaction of the alcohol with acetic acid.

5. The method according to claim 1, wherein the organic alcohol is a butanol.

6. Tim method according to claim 1, wherein the alcohol is selected from n-butanol, s-butanol and i-butanol.

7. The method according to claim 1, further comprising the step of flashing the weak acid stream prior to feeding it to the esterification reactor, thereby supplying vapor phase acetic acid and steam to the esterification reactor and concurrently removing by-products.

8. The method according to claim 1, wherein the pyrolysis step is catalyzed by
   (i) a phosphate catalyst which is subsequently neutralized with ammonia or
   (ii) an ammonium phosphate catalyst.

9. The method according to claim 8, wherein the catalyst is triethyl phosphate.

10. The method according to claim 8, wherein the catalyst is diammonium phosphate.

11. The method according to claim 8, further comprising the step of removing ammonium salts from the weak acid aqueous stream.

12. The method according to claim 11, wherein the step of removing ammonium salts from the weak acid stream includes treating the weak acid stream with a mineral acid.

13. The method according to claim 12, wherein the mineral acid is phosphoric acid.

14. The method according to claim 1, wherein the weak acid aqueous stream has an acid content of from about 10 to about 90 weight percent.

15. The method according to claim 1, wherein the weak acid aqueous stream has an acid content of from about 30 to bout 70 weight percent.

16. The method according to claim 1, wherein the weak acid aqueous stream has an acid content of from about 40 to bout 60 weight percent.

17. The method according to claim 1, wherein the step of pyrolizing the acetic acid is carried out at a temperature of from about 720° C. to about 775° C.

18. The method according to claim 1, wherein the ketene is reacted with acetic acid in the presence of ammonia.

19. A method of co-producing acetic anhydride and an acetate ester comprising:
   (a) pyrolizing acetic acid at elevated temperature to produce a first ketene stream, the first ketene stream being a vapor phase stream comprising ketene, acetic acid and water;
   (b) cooling the first ketene steam to condense acetic acid and water therefrom, thereby generating
      (i) a weak acid aqueous steam and
      (ii) a ketene feed steam; (c) feeding the ketene feed stream to an acetic anhydride reactor where the ketene is reacted with acetic acid to produce acetic anhydride;
   (d) concurrently with step (c), feeding the weak acid aqueous stream to an esterification reactor wherein acetic acid in the weak acid stream is reacted with an organic alcohol to produce an acetate ester in an esterification medium, wherein the organic alcohol forms acetic acid esters which esters and optionally alcohols provide azeotropic mixtures with water; and
   (e) azeotropically separating the acetate ester so formed from the esterification medium.

20. A method of co-producing acetic anhydride and en acetate ester comprising:
  (a) pyrolizing acetic acid at elevated temperature to produce a first ketene stream, the first ketene stream being a vapor phase stream comprising ketene, acetic acid and water;
  (b) cooling the first ketene stream to condense acetic acid and water therefrom, thereby generating
    (i) a weak avid aqueous stream and
    (ii) a ketene feed stream;
  (c) feeding the ketene feed stream to an acetic anhydride reactor where the ketene is reacted with acetic acid to produce acetic anhydride;
  (d) concurrently with step (c), feeding the weak acid aqueous stream to an esterification reactor wherein acetic acid in the weak acid stream is reacted with an organic alcohol to produce an acetate ester in an esterification medium, wherein the organic alcohol is selected from organic alcohols which
    (i) form acetate esters which esters and optionally alcohols provide azeotropic mixtures with water and
    (ii) wherein the azeotropic mixtures have a water content greater than the amount of water generated by reaction of the alcohol with acetic acid; and
  (a) azeotropically separating the acetate ester so formed from the esterification medium.

* * * * *